US00PP31560P2

(12) United States Plant Patent

Lintott et al.

(10) Patent No.: US PP31,560 P2
(45) Date of Patent: Mar. 17, 2020

(54) *LEUCANTHEMUM* PLANT NAMED 'REAL DEAL'

(50) Latin Name: ***Leucanthemum* x *superbum***
Varietal Denomination: Real Deal

(71) Applicants: Jennifer Muriel Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 0 days.

(21) Appl. No.: 16/501,889

(22) Filed: Jun. 27, 2019

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
CPC ..... A01H 5/02; A01H 6/14
See application file for complete search history.

*Primary Examiner* — Annette H Para
(74) *Attorney, Agent, or Firm* — Barbara Campbell; Cochran Freund & Young LLC

(57) ABSTRACT

A new variety of *Leucanthemum* plant named 'Real Deal' that is distinguishable by tight clumping basal branching and upright plant habit, double inflorescences consisting of inner whorls of golden-yellow ray florets and outer whorls of cream or pale-yellow ray florets which are presented horizontally and downwards. Flowering of 'Real Deal' commences in late June and continues until October on plants which are 40 cm in height and 35 cm in width after 1 year of growth from an initial cutting, is disclosed.

2 Drawing Sheets

Genus and species: *Leucanthemum* x *superbum*.
Variety denomination: 'Real Deal'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Deal'. This application is co-pending with the application for the inventors' variety of *Leucanthemum* plant named 'Real Snowball'.

*Leucanthemum* is a genus within the family Asteraceae in which the commonly referred to "flower" is botanically the inflorescence which is comprised of outer showy ray florets surrounding smaller disc florets.

'Real Deal' arose and was selected from an ongoing breeding program which is conducted by the inventors at the inventors' nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Deal' is a seedling selection that resulted from the controlled pollination in 2011 of a single plant of the inventors' proprietary *Leucanthemum* seedling code 'L1008-4' (unreleased and unpatented) as the female parent, using pollen from a single plant of the inventors' proprietary *Leucanthemum* seedling code 'L1122-17' (unreleased and unpatented) as the male parent. The inventors selected 'Real Deal' in 2012 for its combination of tight clumping basal branching and upright habit, domed button-shaped inflorescences which are cream and golden-yellow in color, and held on very strong flower stems.

'Real Deal' was first asexually propagated by the inventors in West Sussex, United Kingdom in 2014 using the method of vegetative division and subsequently by basal shoot cuttings. Since that time under careful observation 'Real Deal' has been determined uniform, stable and true to type in subsequent generations of asexual propagation via basal shoot cuttings and division.

SUMMARY

The following traits have been repeatedly observed and represent the distinguishing characteristics of 'Real Deal'. In combination these traits set 'Real Deal' apart from all other existing varieties of *Leucanthemum* known to the inventor. 'Real Deal' has not been tested under all possible conditions and phenotypic differences may be observed with variations in environmental, climatic, and cultural conditions, however, without any variance in genotype.

1. 'Real Deal' exhibits tight clumping basal-branching and an upright plant habit.
2. The foliage of 'Real Deal' is long and narrow.
3. A fully expanded inflorescence of 'Real Deal' is 5.5 cm to 6.0 cm in diameter and is comprised of ray florets arranged around a central disc.
4. The ray florets of 'Real Deal' are arranged in multiple concentric whorls.
5. The inner (upper) whorls of the ray florets of 'Real Deal' are golden-yellow in color and are presented upwards.

6. The outer (lower) whorls of the ray florets of 'Real Deal' are cream or pale yellow in color and are presented horizontally or reflexed downwards.
7. The inflorescences of 'Real Deal' are carried on a very strong, stiff stems.
8. Flowering of 'Real Deal' commences in late June and continues until October.
9. After one year of growth in a 2-gallon container, or planted in the ground, a plant of 'Real Deal' is 40 cm in height and 35 cm in width.
10. 'Real Deal' is hardy in USDA Zone 5 (−20° F. or −28° C.).

BRIEF DESCRIPTION OF THE PHOTOGRAPHS

The accompanying color photographs were taken in July 2018 in Oxnard, Calif. The photographs illustrate the overall appearance of 'Real Deal' showing the color of foliage and inflorescence as true as is reasonably possible to obtain in color reproductions of this type. The illustrated plants had been grown in 2-gallon containers out of doors, without any pruning or use of chemical growth regulators. The colors in the photographs may differ from color values cited in the detailed botanical description, which accurately describe the actual color of 'Real Deal'.

BOTANICAL DESCRIPTION OF THE PLANT

Figure 1:
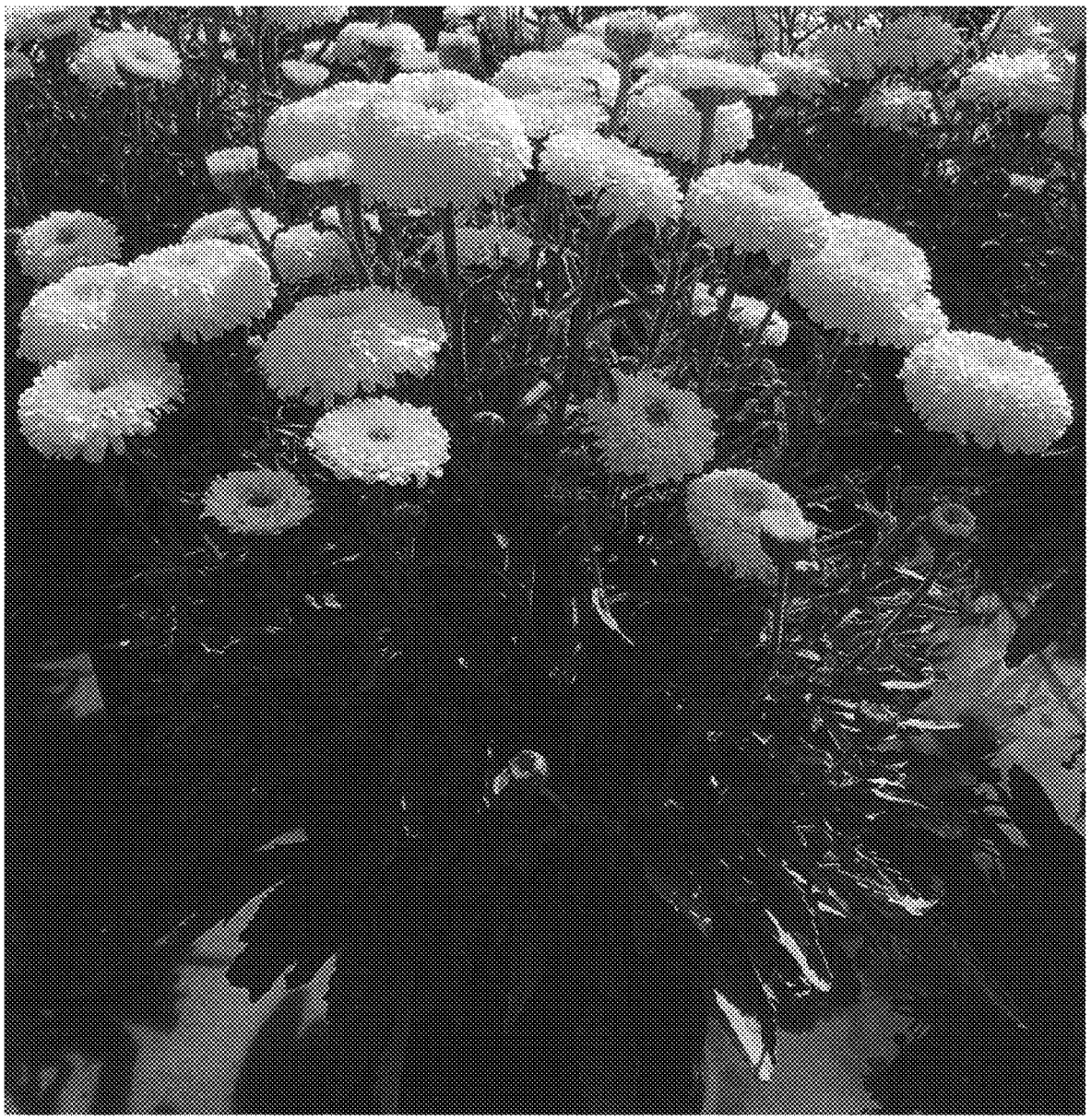
FIG. 1 illustrates, in the foreground, an eighteen-month-old plant of 'Real Deal' (from initial cuttings) which is growing outdoors in a 2-gallon container.
Figure 2:
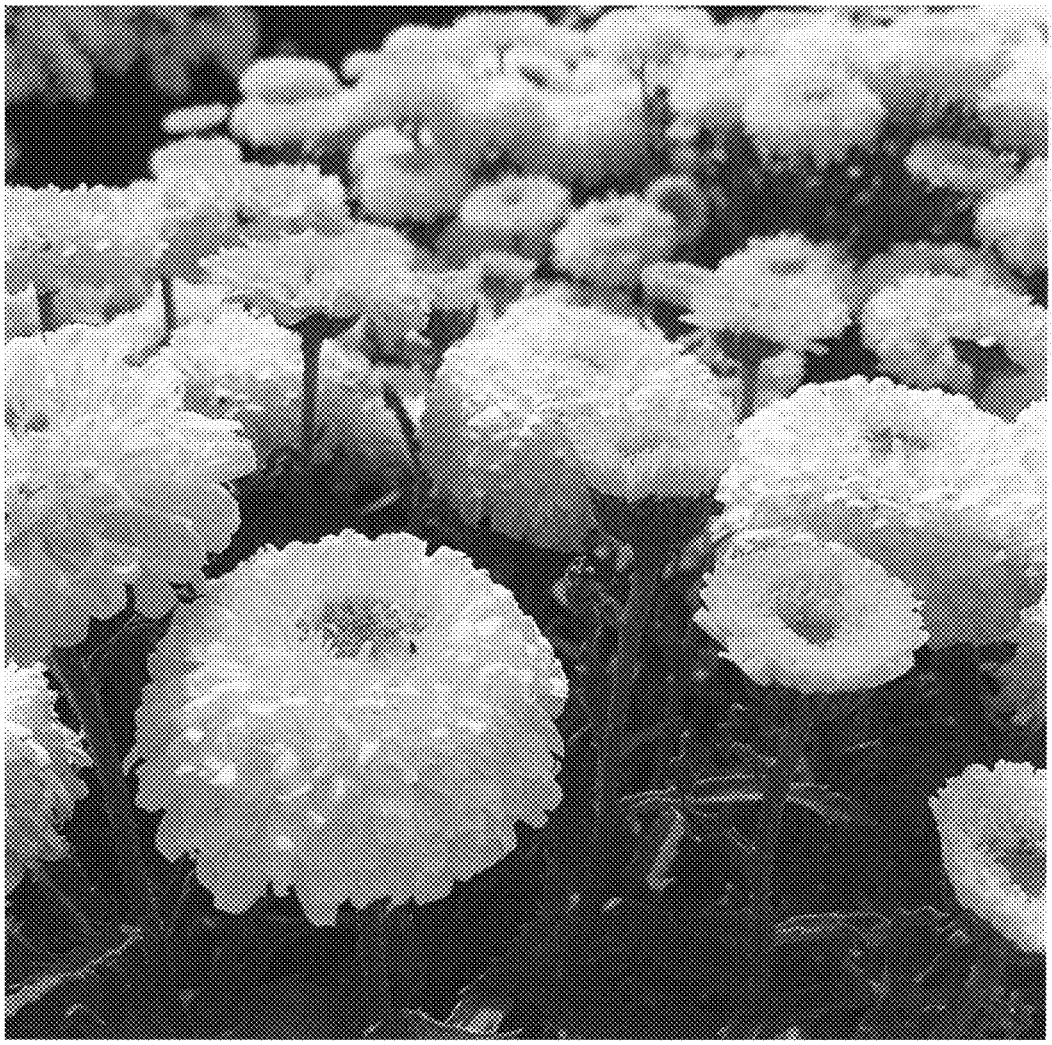
FIG. 2 depicts a close-up view of the inflorescences of 'Real Deal'.

The following is a detailed botanical description of the new variety 'Real Deal'. Observations, measurements, values and comparisons were collected in Santa Barbara, Calif. during late June 2019, from a 1-year old plant growing outdoors in 2 gallon container. Color determinations are made in accordance with The 2007 Royal Horticultural Society Colour Chart from London, England, except where general color terms of ordinary dictionary significance are used.

Botanical classification:

*Family.*—Asteraceae (formerly Compositae).
*Genus.*—*Leucanthemum.*
*Species.*—x *superbum.*
*Denomination.*—'Real Deal'.
*Common name.*—Shasta daisy.
*Habit.*—Vigorous basal-branching and upright growth habit.
*Commercial category.*—Perennial.
*Use.*—For garden and landscape.
*Suggested commercial container size.*—4-inch, 1-gallon, 2-gallon containers.
*Parentage.*—*Leucanthemum* x *superbum* 'Real Deal' is a seedling selection resulting from the controlled cross-pollination of the following parents: Male parent: Inventors' proprietary *Leucanthemum* seedling code 'L1122-17'. Female parent: Inventors' proprietary *Leucanthemum* seedling code 'L1008-4'.
*Propagation method.*—Basal shoot cuttings and division.
*Rooting system.*—Fine and fibrous.
*Vigor.*—Vigorous.
*Time to develop roots* (*range*).—14 to 20 days are needed for an initial cutting to develop roots.
*Temperature to develop roots* (*range*).—The recommended air temperature is 20° C. to 21° C.
*Crop time* (*range*).—7 to 8 months to produce a flowering plant in a 1-gallon container starting from a rooted cutting. 10 months to produce a full plant in a 2-gallon container.
*Plant dimensions* (*one year*).—40 cm in height and 35 cm in width.
*Cultural requirements.*—Grow in full sun and rich, moist moderately fertile well-draining soil.
*Pest or disease resistance and susceptibility.*—No specific disease or pest resistance or susceptibility has been observed or is known to the inventor.
*Hardiness.*—USDA Zone 5.

Stem:

*Branching.*—Basal.
*Color.*—187A.
*Dimensions.*—Length, 15.0 cm; diameter (close to soil surface), 1.0 cm.
*Shape.*—Cylindrical.
*Surface.*—Smooth, glabrous.

Foliage:

*Type* (*division*).—Simple.
*Arrangement.*—Opposite.
*Internode length* (*range*).—2.5 cm to 3.0 cm.
*Margin.*—Mostly regularly dentate; teeth spaced at approximately 4 mm intervals, depth 3 mm.
*Apex.*—Acute.
*Base.*—Attenuate.
*Leaf attachment.*—Sessile.
*Leaf color* (*both surfaces*).—137B.
*Leaf shape.*—Lanceolate.
*Leaf dimensions* (*lower, oldest, leaves*).—12 cm in length, 1.5 cm to 2.2 cm in width.
*Leaf dimensions* (*upper, newest, leaves*).—5 cm to 7 cm in length, 1.0 cm to 1.5 cm in width.
*Leaf venation.*—Pinnate.
*Vein color* (*both surfaces*).—137B.
*Leaf surface* (*adaxial surface*).—Glabrous, sparsely finely pubescent, hairs very short, color silver-grey.
*Leaf surface* (*abaxial surface*).—Glabrous, pubescent, hairs fine, approximately 1 mm in length, color silver-grey. Hairs more numerous along raised abaxial vein midrib.

Inflorescence:

*Inflorescence type.*—Capitulum, flattened dome, consisting of ray florets and disc florets.
*Inflorescence quantity* (*average*).—30 (including colored buds).
*Inflorescence diameter* (*fully opened*).—5.5 cm to 6.0 cm.
*Inflorescence depth.*—4.5 cm.
*Inflorescence aspect.*—Upright.
*Inflorescence colors* (*when fully developed*).—Outer (lower) ray florets: NN155A. Inner (nearest to disc) ray florets: 12A. Central disc: 17B to 17C.
*Fragrance.*—Characteristic of freshly cut grass.
*Blooming season.*—Late June to October.
*Lastingness of inflorescence* (*range*).—10 to 14 days on the plant; ray florets are persistent.

Bud:

*Bud dimensions.*—0.75 cm in height and 1.25 cm in diameter.
*Bud shape.*—Flattened sphere.

*Bud color.*—147B, apex (cluster of involucral bracts) 178A.
*Bud surface.*—Glabrous.

Peduncle:
*Peduncle shape.*—Cylindrical.
*Peduncle length.*—16.0 cm to 35.0 cm.
*Peduncle diameter.*—4.0 mm to 6.0 mm.
*Peduncle surface.*—Furrowed, minutely pubescent, hair color silver-grey.
*Peduncle strength.*—Very strong and stiff.
*Peduncle color.*—187A becoming 144B closer to the inflorescence.

Peduncle bracts:
*Arrangement.*—Single, alternate, rotate around peduncle.
*Quantity.*—15-20, spaced between 1 cm and 2 cm apart.
*Attachment.*—Sessile.
*Shape.*—Lanceolate.
*Margin.*—Minutely dentate.
*Apex.*—Acute.
*Base.*—Attenuate.
*Color* (*both surfaces*).—137B.
*Dimensions.*—1.5 cm to 2.2 cm in length, 0.6 cm to 0.8 cm in width.
*Surface* (*adaxial surface*).—Coriaceous.
*Surface* (*abaxial surface*).—Smooth, glaucous.

Ray florets:
*Ray floret arrangement.*—Whorled, consisting of five or more concentric whorls of broad strap-like ray florets.
*Shape.*—Quilled; corolla tube subtends single ligule or petal.
*Quantity.*—200 to 240 per inflorescence.
*Aspect.*—Inner ray florets (nearest to disc) upright; outer ray florets horizontal to downward facing.
*Corolla tube dimensions.*—3 mm in length, 1 mm in diameter.
*Corolla tube color.*—144C.

Ray floret petals:
*Shape.*—Strap-like, longitudinally furrowed forming three to five petal lobes.
*Surface* (*both surfaces*).—Glabrous.
*Apex.*—Emarginate (3-5 lobed).
*Margin.*—Entire.
*Dimensions.*—Inner ray florets (nearest to disc): 0.8 cm to 1.5 cm in length and 3 mm to 5 mm in width. Outer ray florets: 2.0 cm to 2.5 cm in length, 5 mm to 9 mm in width.
*Color* (*both surfaces*).—Inner ray florets, 12A; outer ray florets: NN155A.

Involucral bracts:
*Quantity* (*average*).—40-45 per inflorescence, overlapping, fused at base.
*Bract color* (*abaxial and adaxial surfaces*).—139C.
*Bract length.*—9 mm to 11 mm.
*Bract width.*—3.0 mm.
*Bract apex.*—Rounded with tiny cilia.
*Bract base* (*range*).—Rounded.
*Bract surface* (*both surfaces*).—Glabrous.
*Bract shape.*—Lanceolate.
*Bract margin.*—Entire, smooth, color 178A.

Disc floret:.
*Disc diameter.*—2.6 cm to 3.0 cm.
*Disc floret quantity* (*average*).—Approximately 220 to 250 per inflorescence, massed at center of receptacle.
*Disc floret color.*—17B to 17C.
*Disc floret dimensions.*—6 mm to 7 mm in length, 1 mm in diameter.
*Disc floret shape.*—Tubular.
*Disc floret petal quantity.*—Ranges from 3 to 5 in number, basally fused.
*Disc floret petal dimensions.*—3 mm in length, 0.75 mm to 1.0 mm in width.
*Disc floret petal color.*—17B-17C.
*Disc floret petal apex.*—Acute.
*Disc floret petal base.*—Truncate.
*Disc floret corolla tube.*—4 mm in length, 0.75 mm in diameter, color 145B to 145C.

Reproductive organs:
*Ray flowers.*—Androecium (stamens, anthers, filaments, pollen): Absent. Pistil: One, 3 mm in length, hair-like, diameter less than 0.2 mm, color light brown. Stigma: 2 mm in length, hair-like, diameter less than 0.2 mm, color light brown. Ovary (observed immature only): Superior, globose, less than 1 mm in diameter, color 145C.
*Disc flowers.*—General: Stigma, style, and ovary not observed. Stamens: 5 probably fused appearing as one, length 1 mm, color 175A. Pollen: None observed. Pistil: 1, less than 1 mm in length, stigma, style, ovary not observed.

Seed: None observed to date.

COMPARISON WITH PARENTAL LINES AND KNOWN VARIETY

In comparison with the female parent, seedling code 'L1008-4', 'Real Deal' is smaller and more compact in size and habit, and bears smaller flowers which are golden yellow and cream-yellow in color, compared with the white flowers of the female parent. In comparison with the male parent, seedling code 'L1122-17', 'Real Deal' is smaller and more compact in size and habit, and bears deeper yellow-colored flowers than the pale cream flowers of the male parent. In addition, 'Real Deal' flowers over a longer period than the male parent.

The commercial varieties of *Leucanthemum* which the inventors consider to most closely resemble 'Real Deal' are the inventors' variety of *Leucanthemum* Plant Named 'Real Dream' (U.S. Plant Pat. No. 25,664), and *Leucanthemum* Plant Named 'Luna' (U.S. Plant Pat. No. 27,037).

In comparison with 'Real Dream', although the plant habits and sizes are very similar, the arrangement of the petals (ray florets) is markedly different. Whereas the petals (ray florets) of 'Real Deal' are arranged in multiple whorls conferring a double-flowered appearance, the petals of 'Real Dream' are arranged in 2 or 3 whorls conferring a single-flowered appearance. In addition, the color of the inflorescence of 'Real Deal' is a combination of cream-yellow (lower petals) and golden-yellow (upper petals), whereas the inflorescence of 'Real Dream' is cream-yellow throughout.

In comparison with 'Luna', 'Real Deal' is a smaller plant overall (height and width) and bears narrower foliage. In addition, the inventors have observed that 'Real Deal' is approximately 10 days later into flower than 'Luna'.

We claim:

1. A new and distinct variety of *Leucanthemum* plant named 'Real Deal' as described and illustrated herein.

* * * * *